(12) United States Patent
Harrison et al.

(10) Patent No.: US 8,915,915 B2
(45) Date of Patent: Dec. 23, 2014

(54) APPARATUS AND METHODS FOR MAGNETIC ALTERATION OF ANATOMICAL FEATURES

(71) Applicant: The Regents of the University of California, Oakland, CA (US)

(72) Inventors: Michael R. Harrison, San Francisco, CA (US); Dillon A. Kwiat, San Francisco, CA (US); Richard J. Fechter, San Rafael, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/155,509

(22) Filed: Jan. 15, 2014

(65) Prior Publication Data

US 2014/0128868 A1 May 8, 2014

Related U.S. Application Data

(63) Continuation-in-part of application No. 13/893,541, filed on May 14, 2013, which is a continuation of application No. 11/677,700, filed on Feb. 22, 2007, now Pat. No. 8,439,915, which is a continuation-in-part of application No. 11/431,416, filed on May 9, 2006, now abandoned, which is a continuation-in-part of application No. 10/954,995, filed on Sep. 29, 2004, now Pat. No. 8,043,290.

(51) Int. Cl.
A61B 17/66 (2006.01)
A61B 17/70 (2006.01)
A61B 17/80 (2006.01)
A61B 17/68 (2006.01)

(52) U.S. Cl.
CPC ............. *A61B 17/66* (2013.01); *A61B 17/7016* (2013.01); *A61B 17/8004* (2013.01); *A61B 2017/681* (2013.01)
USPC .......................................................... 606/60

(58) Field of Classification Search
USPC ................. 606/60, 62–68, 90, 105, 246–279, 606/300–331
See application file for complete search history.

(56) References Cited

U.S. PATENT DOCUMENTS

| 6,033,412 A | * | 3/2000 | Losken et al. ................. 606/105 |
| 6,849,076 B2 | * | 2/2005 | Blunn et al. .................. 606/105 |
| 8,439,915 B2 | * | 5/2013 | Harrison et al. ................ 606/60 |
| 2006/0047282 A1 | * | 3/2006 | Gordon ........................... 606/61 |

\* cited by examiner

*Primary Examiner* — Christopher Beccia
(74) *Attorney, Agent, or Firm* — Lumen Patent Firm

(57) ABSTRACT

Systems and methods are disclosed for manipulating an anatomical feature within the body of the patient.

5 Claims, 5 Drawing Sheets

APPARATUS AND METHODS FOR MAGNETIC ALTERATION OF ANATOMICAL FEATURES

CROSS-REFERENCE TO RELATED APPLICATIONS

This application is a continuation-in-part (CIP) of U.S. patent application Ser. No. 13/893,541 filed May 14, 2013, which is incorporated herein by reference.

U.S. patent application Ser. No. 13/893,541 filed May 14, 2013 is a continuation of U.S. patent application Ser. No. 11/677,700 filed Feb. 22, 2007, which is incorporated herein by reference.

U.S. patent application Ser. No. 11/677,700 filed Feb. 22, 2007 is a continuation in part (CIP) of U.S. patent application Ser. No. 11/431,416 filed May 9, 2006, which is incorporated herein by reference.

U.S. patent application Ser. No. 11/431,416 filed May 9, 2006 is a continuation in part (CIP) of U.S. patent application Ser. No. 10/954,995 filed Sep. 29, 2004, which is incorporated herein by reference.

FIELD OF THE INVENTION

This invention pertains generally to apparatus and methods for magnetically manipulating body structures and more particularly to performing corrective procedures on a patient via incremental magnetic loading.

BACKGROUND OF THE INVENTION

Anatomical deformities occur in the general populous in a number of different forms and from a variety of causes. Examples of skeletal deformities include pectus excavatum, scoliosis, club feet, and numerous forms of skeletal dysplasia. These conditions are treated in a variety of different manners from braces to surgery, with sometimes minimal efficacy.

The defect known as pectus excavatum, or funnel chest, is a congenital anomaly of the anterior chest wall. The excavatum defect is characterized by a deep depression of the sternum, usually involving the lower half or two thirds of the sternum, with the most recessed or deepest area at the junction of the chest and the abdomen. The lower 4-6 costal or rib cartilages dip backward abnormally to increase the deformity or depression and push the sternum posterior or backward toward the spine. Also, in many of these deformities, the sternum is asymmetric or it courses to the right or left in this depression. In many instances, the depression is on the right side.

Pectus excavatum with significant deformity occurs in approximately 1 out of every 2000 births. The deformity may be present at birth but is often noted after several years of age and usually worsens during rapid growth around puberty. Because of the pressure of the sternum and cartilages, defect also pushes the midline structures so that the lungs are compressed from side to side and the heart (right ventricle) is compressed. Severe lesions have a major effect on thoracic volume and pulmonary function but the principal motivation for repair is the deformity itself. It does occur in families and thus, is inherited in many instances. Other problems, especially in the muscle and skeletal system, also may accompany this defect. In approximately ⅕ of the patients, scoliosis is present. The regression or any improvement in this defect rarely occurs because of the fixation of the cartilages and the ligaments. When one takes a deep breath or inspires, the defect is usually accentuated.

Pectus excavatum can be repaired surgically using an open approach in which the malformed costal cartilages are resected and the sternum forcibly held in place with a metal strut. In another approach, described in U.S. Pat. No. 6,024,759, the sternum is forced into a corrected position often under great tension, and held in place with a metal strut. Both can achieve good results but at the cost of considerable morbidity: an operation under general anesthesia followed by a 4-7 day hospital stay required for pain control usually by continuous epidural analgesia. Several more weeks of moderate to severe discomfort are typical and complications from the sternum held forcibly against the metal strut are not infrequent. It is necessary to leave the bar in place for a year or more before it is removed in another procedure. Total cost usually reimbursed by third party payers averages more than $30,000.

The problem with all currently available pectus excavatum surgical repairs is that they attempt to achieve immediate total correction and fixation often under considerable tension. A better approach would be the gradual step-by-step correction of the deformity by applying a smaller force over a longer period of time.

Another skeletal deformity, scoliosis, is a condition in which an individual has an abnormal spine curvature. Generally, some curvature in the neck, upper trunk and lower trunk is normal. However, when there are abnormal side-to-side (lateral) curves in the spinal column, the patient is generally diagnosed as having as scoliosis.

Orthopaedic braces are typically used to prevent further spinal deformity in children with curve magnitudes within the range of 25 to 40 degrees. If these children already have curvatures of these magnitudes and still have a substantial amount of skeletal growth left, then bracing is a viable option. The intent of bracing, however, is to prevent further deformity, and is generally not used to correct the existing curvature or to make the curve disappear.

Surgery is an option used primarily for severe scoliosis (curves greater than 45 degrees) or for curves that do not respond to bracing. The two primary goals for surgery are to stop a curve from progressing during adult life and to diminish spinal deformity.

Although there are different techniques and methods used today for scoliosis surgery, all of them involve fairly invasive procedures with considerable patient morbidity. One frequently performed surgery involves posterior spinal fusion with instrumentation and bone grafting, which is performed through the patient's back.

During this surgery, the surgeon attaches a metal rod to each side of the patient's spine by anchors attached to the vertebral bodies. The spine is then fused with a bone graft. The operation usually takes several hours and the patient is typically hospitalized for a week or more. Most patients are not able to return to school or for several weeks after the surgery and cannot perform some pre-operative activities for up to four to six months.

Another surgery option for scoliosis is an anterior approach, wherein the surgery is conducted through the chest walls instead of entering through the patient's back. During this procedure, the surgeon makes incisions in the patient's side, deflates the lung and removes a rib in order to reach the spine. The anterior spinal approach generally has quicker patient rehabilitation, but usually requires bracing for several months after this surgery.

For these reasons, it would be desirable to provide improved apparatus and methods for repositioning bone structures, by applying a corrective force to the bone structure, which could be gradually adjusted much like orthodontic tooth braces.

It would be further desirable to provide a device that applies a corrective force to reposition a body member without a mechanical force that requires piercing of the skin, thereby limiting the specter of infection and wound problems.

In addition, it would be desirable to provide a device for repositioning bones structures having tension-sensing technology to allow measurement of the force applied to correct all types of asymmetric deformities and allow protection of skin against pressure damage.

It would further be desirable to provide improved devices and methods for minimally invasively treating pectus excavatum.

In addition, it would be desirable to provide improved devices and methods for minimally invasively treating scoliosis.

At least some of these objectives will be met with the inventions described hereinafter.

SUMMARY OF THE INVENTION

Systems and methods are disclosed for manipulating an anatomical feature within the body of the patient. An implant such as an internal jackscrew is implanted at the anatomical and has first and second attachment points that secure to spaced-apart locations on the anatomical feature, an internal rotor coupled to the jackscrew, and is configured to drive motion of the jackscrew to manipulate the anatomical feature. The system further includes an external rotor that is magnetically coupled to the internal rotor such that rotation of the external rotor at an exterior location to the patient's body affects a corresponding internal rotation of the internal rotor to manipulate the anatomical feature.

DETAILED DESCRIPTION

Figure 1:
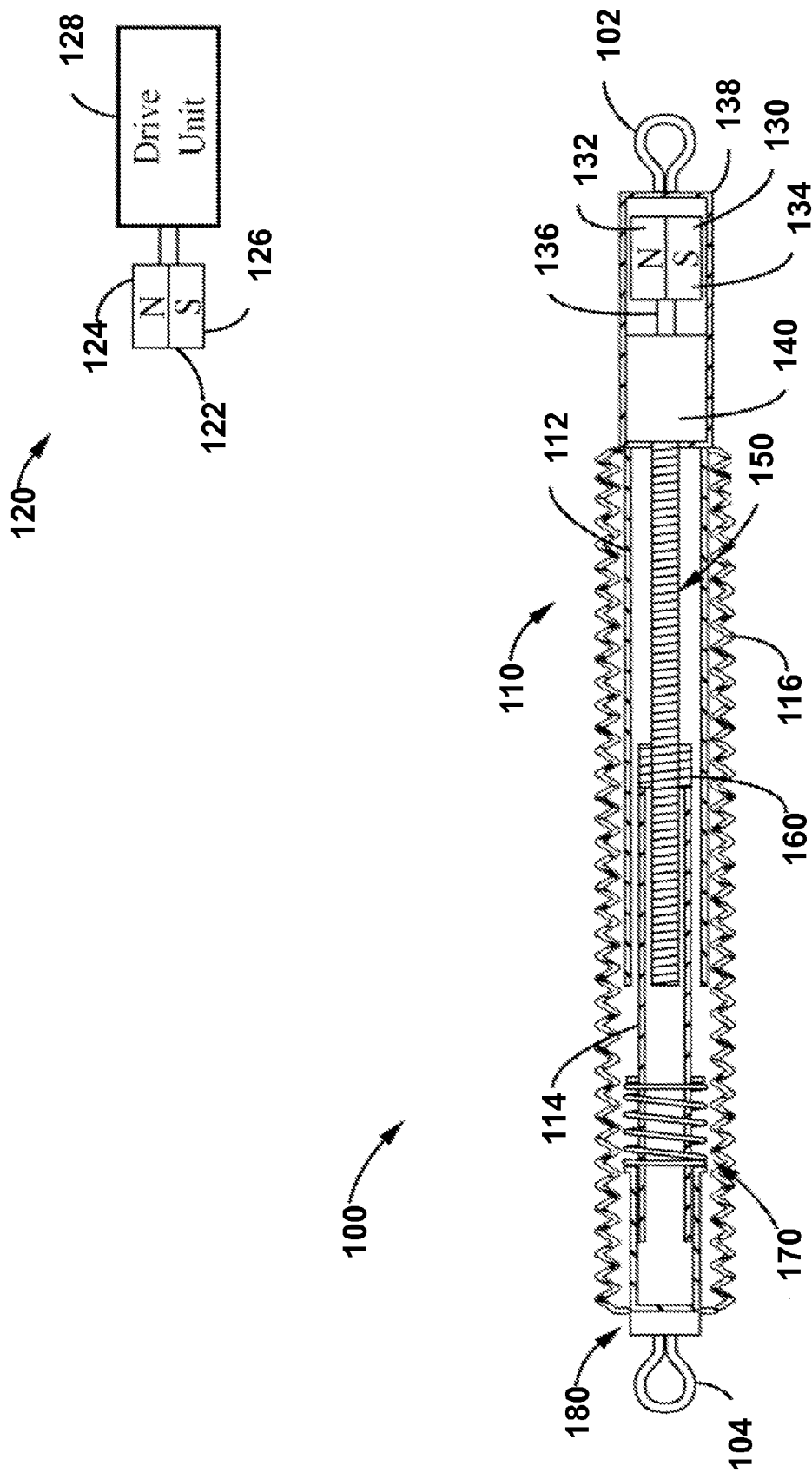
FIG. 1 shows a view of an internal jackscrew assembly according to an exemplary embodiment of the invention.

FIG. 1 shows an embodiment of a repulsion system 100. The system 100 includes a magnetically coupled implantable jackscrew assembly 110 that is magnetically driven by an external drive assembly 120. The jackscrew assembly 110 comprises a first member 112 and second member 114 housed within a hermetically sealed bellows 116. The first and second members 112, 114 are coupled to allow linear motion with respect to each other to apply a repulsive force to respective attachment points 102 and 104 that may be attached to one or more body members or body member locations. For example attachment point 102 may be coupled to a first vertebral body, and attachment point 104 may be coupled to a second vertebral body to allow incremental distraction of the spine segments. Attachment point 102 may be coupled to one part of a long bone and attachment point 104 may be coupled to another part of the same long bone to allow incremental distraction and growth of the bone.

The first member 112 is coupled to an internal drive coupling or rotor 130 that is radially magnetized (may also be axially magnetized in an alternative embodiment) into semi-cylindrical halves 132 and 134. The internal rotor 130 is coupled to drive shaft 136 inside end cap 138.

The external drive assembly 120 has an external drive magnet or rotor 122, also being radially magnetized into semi-cylindrical halves 124 and 126. The external rotor 122 is coupled to a high-speed rotational unit 128 (e.g. electric motor or the like) that is capable of rotating magnet 122 at high rpm. The internal and external rotors are polarized such that, when the external drive assembly 120 is positioned with the external rotor 122 at an external location above the patient's skin from the internal rotor 130, rotation of the external rotor 122 causes a proportional rotation in internal rotor 130, which in turn rotates shaft 136. Shaft 136 is coupled to gear reduction unit 140 that facilitates a high ratio gear reduction (e.g. 256:1 or 500:1 or 1024:1) to threaded rod 150. Gear reduction unit 140 allows high speed micro-motion control of the jackscrew assembly 110 via a small input or rotational force from the external rotor 122. The gear reduction unit 140 may comprise a custom made unit or commercially available unit such as Faulhaber Planetary Gearhead 10/1 from MicroMo, Clearwater, Fla.

Female screw thread or nut 160 is attached to second member 114 and is threaded to threaded rod 150 such that rotation of threaded rod 150 causes the first member 112 to separate or converge with respect to second member from 114. Additional force and separation may be achieved by further rotation of external magnet 122.

The second member 112 may optionally be spring loaded with biasing member 170 to create an additional preload between the first and second members. Biasing member 170 may provide a shock absorption component to the assembly for withstanding loading between first and second body members disposed on attachment points 102 and 104. Initial loading to separate attachment points 102 and 104 may soak up some or all of the travel of biasing member 170, depending on the spring rate. However, as the body members associated with attachments points 102 and 104 are gradually manipulated, the travel of biasing member 170 is restored.

FIG. 1 further shows a linear coil-spring design for biasing member 170, however it is contemplated that an elastomer or magnetic repulsion spring (as shown in FIG. 23 in U.S. patent application Ser. No. 11/677,700 filed Feb. 22, 2007) may also be used.

The jackscrew assembly 110 may also comprise a force measurement transducer 180 that measures the force applied to the attachment points 102 and 104. Transducer 180 is configured to take readings of the applied force over time, and may be configured to store them locally on a memory chip or the like, or transmit force data to an external receiving unit via a wireless remote transmission such as RFID, IR or the like. Transducer 180 may also comprise deformable silicon pressure sensing device, such as the Micro Electro Mechanical Systems (MEMS) implant currently be developed by Cleveland Clinic for orthopedic sensing.

Figure 2:
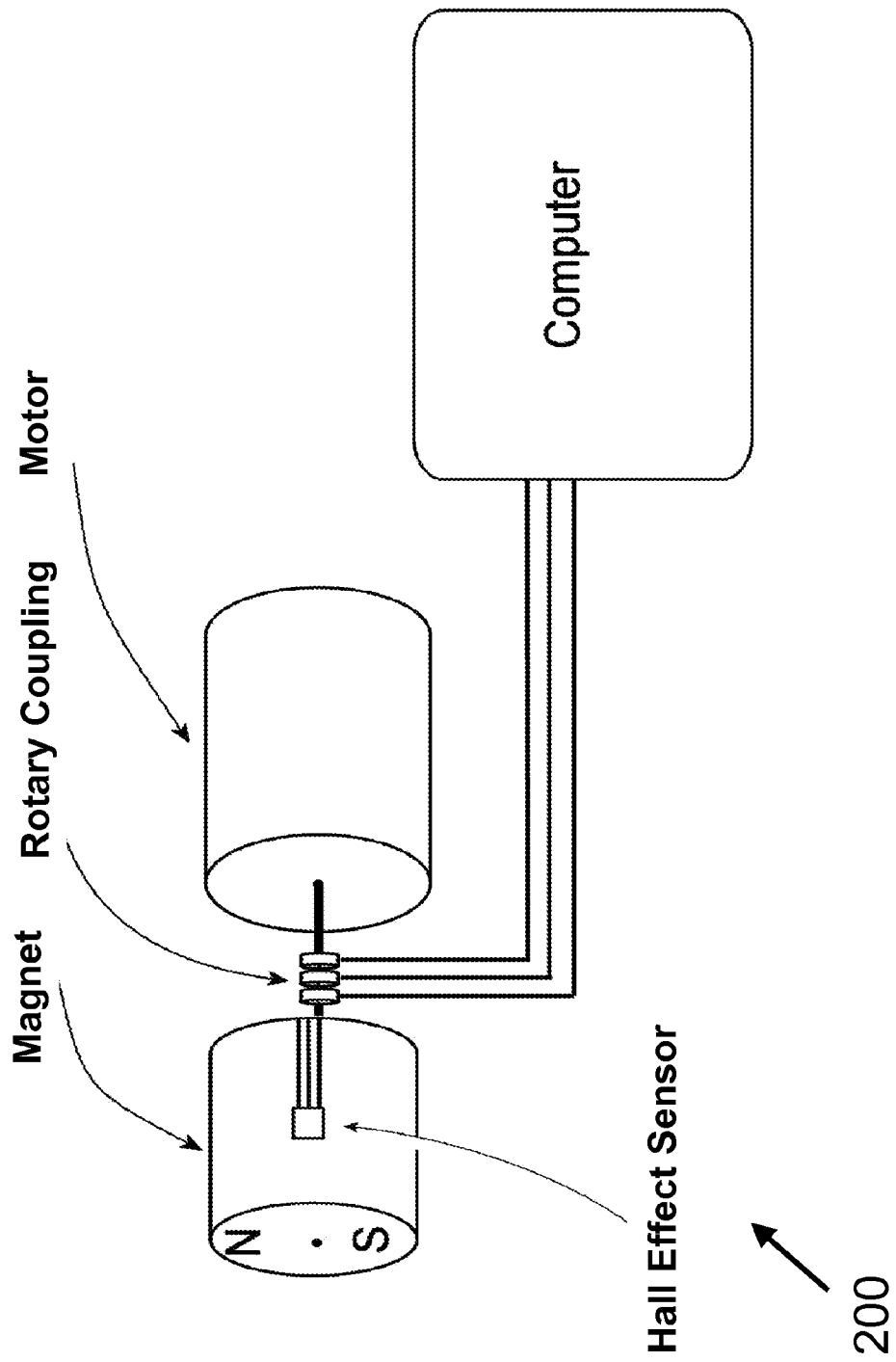
FIGS. 2-5 show sensor mechanisms 200, 300, 400 and 500 according to exemplary embodiments of the invention.

In another embodiment as shown in FIG. 2, a Hall effect sensor arrangement could be used. Hall effect magnetic sensors could be fixed on opposite sides of the magnetic rotor 122 at 180 degrees apart such that the magnetic flux is equal and opposite when not in the presence of the implanted rotor 130. Signals from the sensors are summed, so the flux from the drive rotor 122 is cancelled out, leaving only the signal from the implant rotor. Electronic circuit measures signal and differentiates between coupled and uncoupled states. Electronic control circuit measures rotations of the implant rotor 130 and knowing the gear reduction ratio, calculates the displacement. Circuit could also accept prescription from a doctor and prevents displacement beyond the desired amount.

A single Hall effect sensor could be attached to the drive rotor 122 on a spot where the measured flux is near zero. In the presence of the implant rotor 130, a signal will be present when rotated. Electronic circuit measures signal and differentiates between coupled and uncoupled states, etc. as above.

Figure 3:
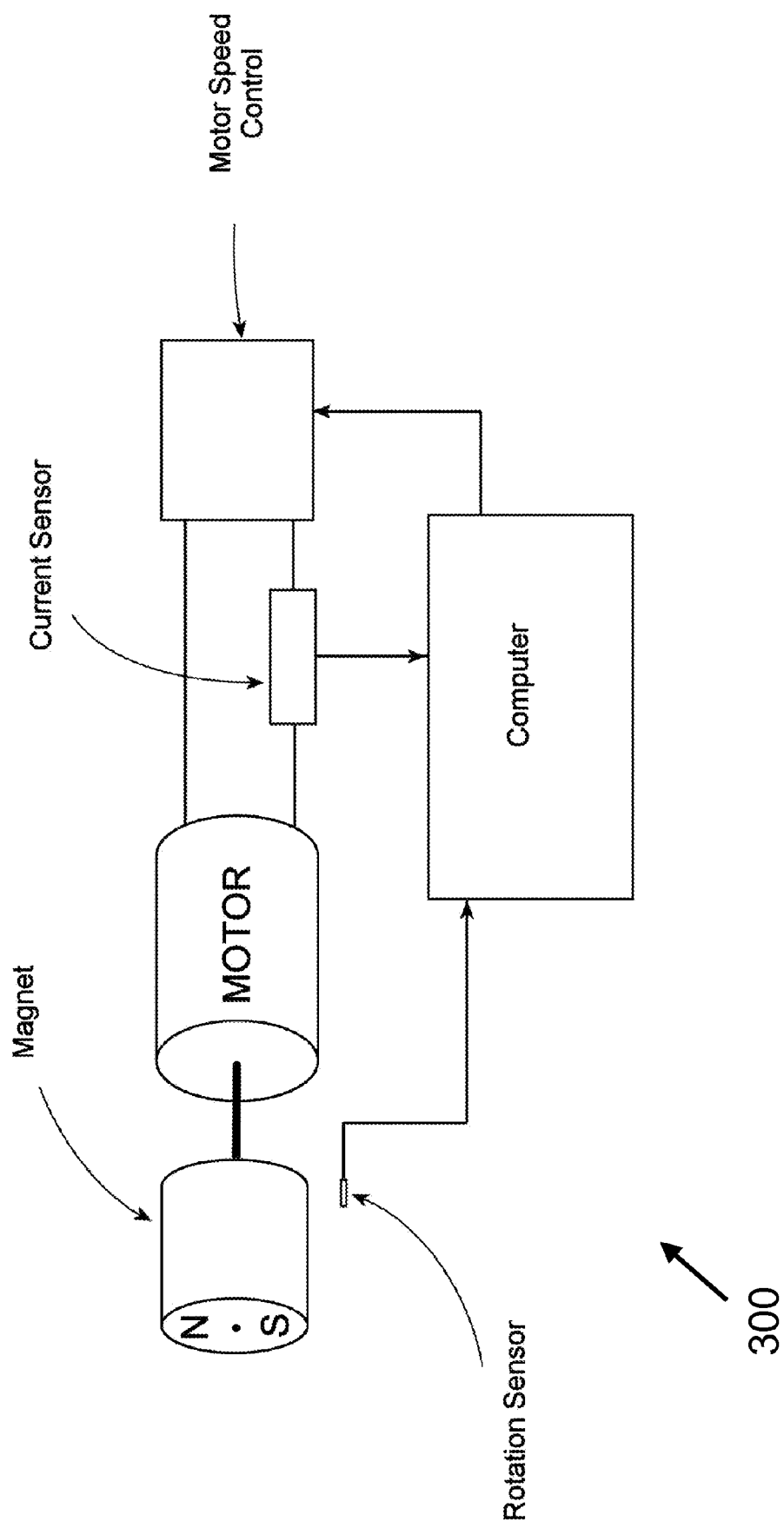

In yet another embodiment as shown in FIG. 3, we consider a torque on the implant rotor 130 to be equal to the torque on the drive rotor 122, averaged over one rotation. Drive rotor 122 torque is measured by measuring the current going to the driver motor. An electronic circuit measures signal and differentiates between coupled and uncoupled states. Electronic control circuit measures rotations of the implant rotor 130 and knowing the gear reduction ratio, calculates the displacement. Circuit also accepts prescription from a doctor and prevents displacement beyond the desired amount. The motor can be a brushed, a brushless, or a stepper motor.

Figure 4:
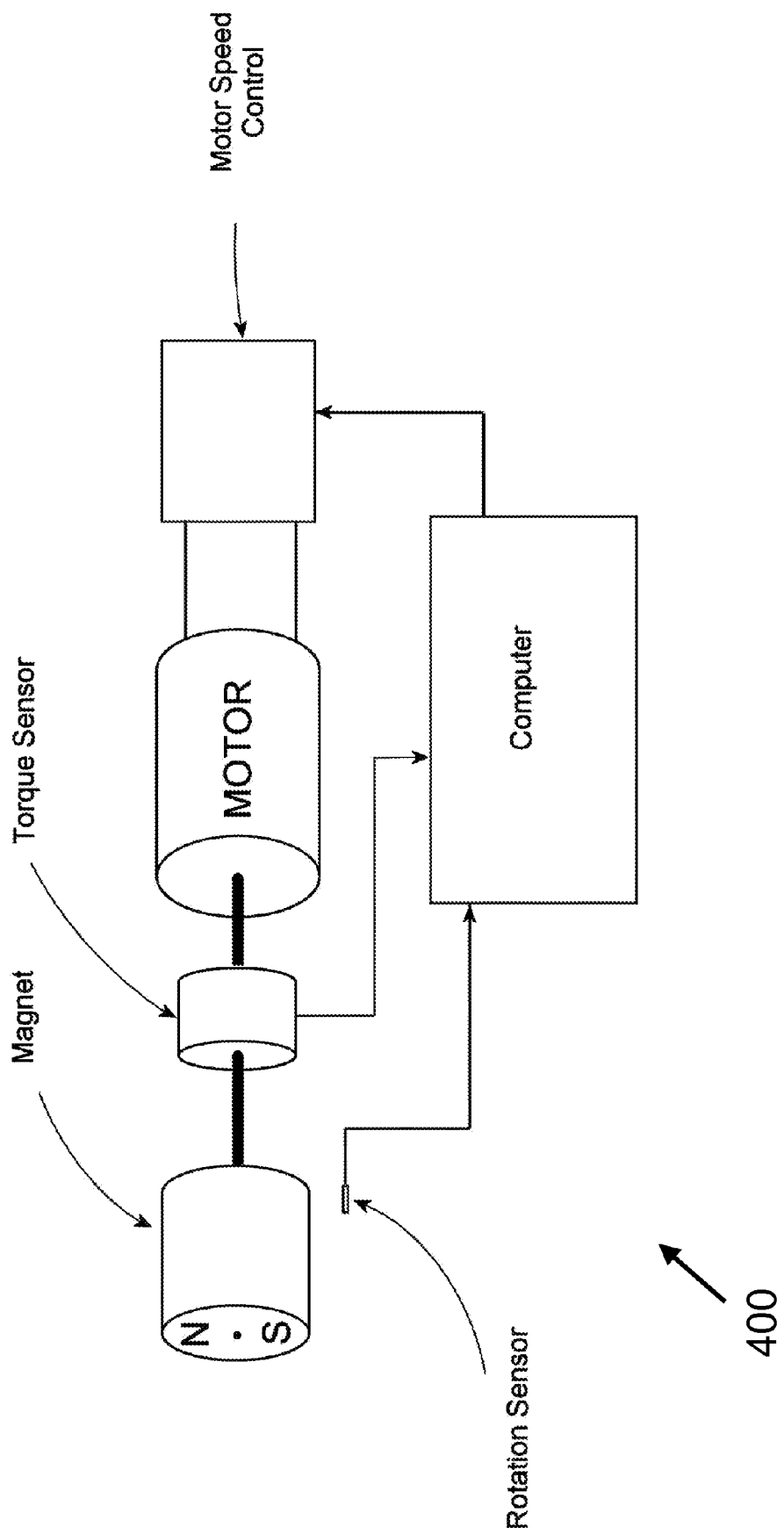

In yet another embodiment as shown in FIG. 4, we consider that the torque on drive rotor 122 is measured by mechanical torque sensor. This could be an elastic coupling between the motor and drive rotor 122 with angular position sensors on both sides of the coupling that sense the amount of 'twist' in the elastic element. Electronic circuit converts angle difference to torque measurement. Electronic circuit measures signal and differentiates between coupled and uncoupled states. Electronic control circuit measures rotations of the implant rotor 130 and knowing the gear reduction ratio, calculates the displacement. Circuit also accepts prescription from a doctor and prevents displacement beyond the desired amount.

Figure 5:
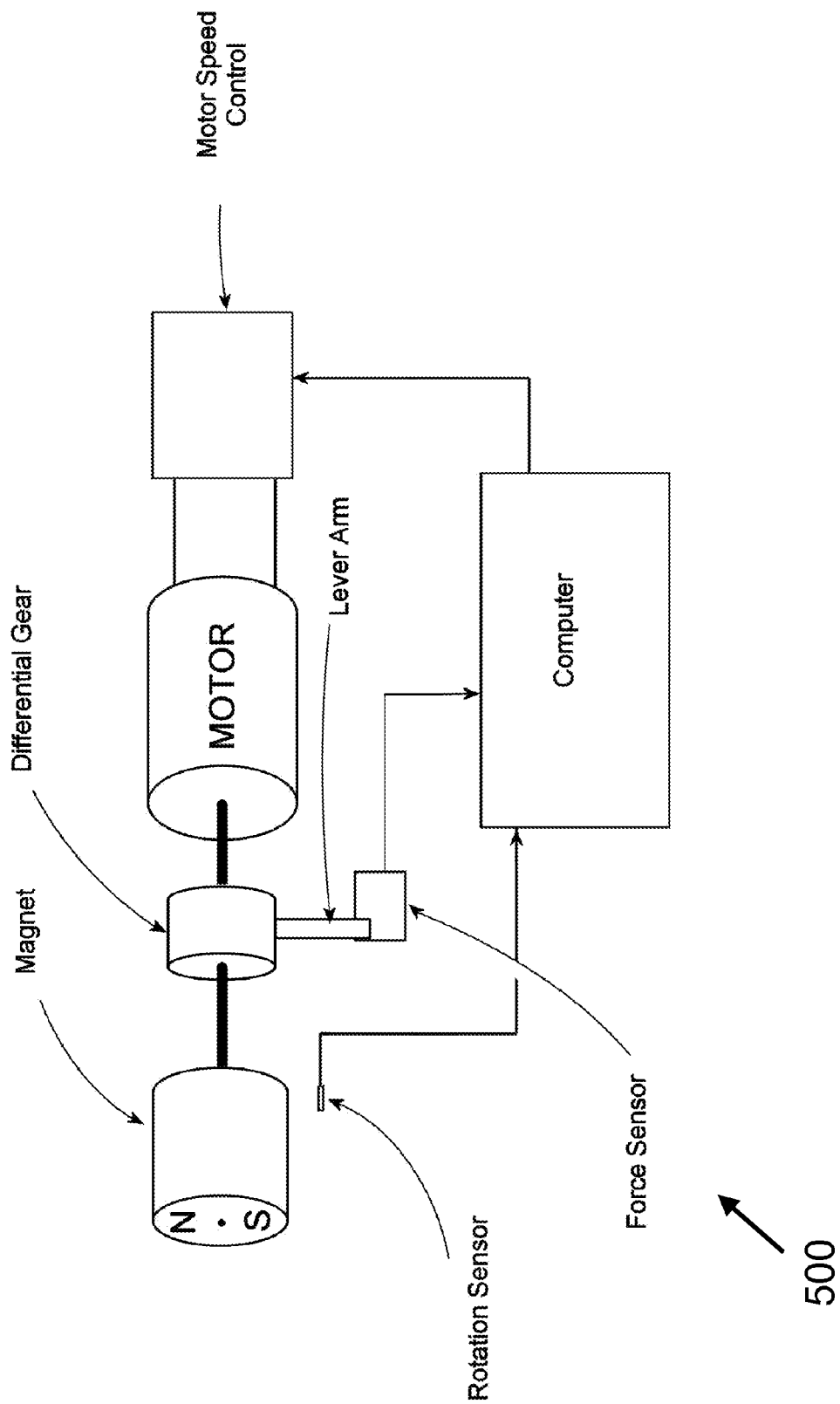

In still another embodiment as shown in FIG. 5, we consider that the torque on the drive rotor 122 is measured by using a differential gear between the motor and drive rotor 122. A force sensing transducer is attached to the mid-point of the differential gear such that the force will be proportional to the drive torque. Electronic circuit measures signal and differentiates between coupled and uncoupled states. Electronic control circuit measures rotations of the implant rotor 130 and knowing the gear reduction ratio, calculates the displacement. Circuit also accepts prescription from a doctor and prevents displacement beyond the desired amount.

Embodiments, teachings, figures and examples are described in U.S. patent application Ser. No. 11/677,700 filed Feb. 22, 2007, which is incorporated herein by reference.

What is claimed is:

1. A body member repulsion device, comprising:
   a. a jackscrew capable of being implanted to a body, wherein said jackscrew comprises a first attachment point capable of attaching to a first member and a second attachment point capable of attaching to a second member;
   b. a biasing member configured to absorb loading between said first member and said second member;
   c. an internal rotary magnet coupler capable of being implanted to said body;
   d. a gear reduction unit coupled between said internal rotary magnet coupler and said jackscrew;
   e. a work conduit, wherein said work conduit is disposed between said internal rotary magnet coupler and said jackscrew;
   f. an external rotary magnet coupler capable of being disposed outside said body and proximal to said internal rotary magnet coupler, wherein said external magnetic coupler is magnetically coupled to said internal magnetic coupler, wherein when work is applied to said external rotary magnet coupler said internal rotary magnet coupler receives said work and conveys said work to said jackscrew through said work conduit, wherein said work applied to said jackscrew moves said first attachment point and said second attachment point, or wherein said work applied to said jackscrew moves said first attachment point or said second attachment point; and
   g. a sensor mechanism to determine displacement between said first member and said second member.

2. The body member repulsion device as set forth in claim 1, wherein said work conduit comprises a flexible shaft.

3. The body member repulsion device as set forth in claim 2, wherein said wherein said flexible shaft is connected to a worm drive disposed in said jackscrew.

4. The body member repulsion device as set forth in claim 1, wherein said internal magnetic coupler comprises an internal magnet.

5. The body member repulsion device as set forth in claim 1, wherein said external magnetic coupler comprises an external magnet.

* * * * *